US00PP20650P2

(12) United States Plant Patent
Gear et al.

(10) Patent No.: US PP20,650 P2
(45) Date of Patent: Jan. 19, 2010

(54) ***AGAPANTHUS* PLANT NAMED 'GOLD STRIKE'**

(50) Latin Name: *Agapanthus inapertus*
Varietal Denomination: GOLD STRIKE

(76) Inventors: Ian Gear, 41 Ashton Fitchett Drive, Brooklyn, Wellington (NZ) 6021; Helen Gear, 41 Ashton Fitchett Drive, Brooklyn, Wellington (NZ) 6021

( * ) Notice: Subject to any disclaimer, the term of this patent is extended or adjusted under 35 U.S.C. 154(b) by 0 days.

(21) Appl. No.: 12/151,952

(22) Filed: May 8, 2008

(51) Int. Cl.
*A01H 5/00* (2006.01)

(52) U.S. Cl. ..... Plt./398

(58) Field of Classification Search ..... Plt./398, Plt./256

See application file for complete search history.

*Primary Examiner*—Annette H Para

(57) ABSTRACT

A new cultivar of *Agapanthus* plant named 'GOLD STRIKE' that is characterized by compact habit, green and gold strap-like leaves, and dark-blue flowers on black stems. In combination these traits set 'GOLD STRIKE' apart from all other existing varieties of *Agapanthus* known to the inventor.

2 Drawing Sheets

Genus: *Agapanthus*.
Species: *inapertus*.
Denomination: 'GOLD STRIKE'.

BACKGROUND OF THE INVENTION

The present invention relates to a new and distinct cultivar of lily-of-the-Nile grown as an ornamental plant for use on patio, deck, and in the landscape. The new cultivar, from the family Liliaceae, is known botanically as *Agapanthus inapertus* and will be hereinafter referred to as 'GOLD STRIKE'.

The new *Agapanthus* cultivar named 'GOLD STRIKE' was discovered in Hamilton, New Zealand as a chance seedling in and amongst a commercially grown crop of *Agapanthus inapertus*. The female parent is an unnamed individual *Agapanthus inapertus* hybrid (unpatented) and the male parent is an unnamed individual *Agapanthus inapertus* hybrid (unpatented). The inventor selected the variety named 'GOLD STRIKE' in 1990 based on the criteria of habit and foliage color. The new variety named 'GOLD STRIKE' yields a range of 4–6 divisions per year.

'GOLD STRIKE' is a hybrid plant exhibiting compact habit, green and gold variegated foliage, and dark-blue flowers on black stems. Cultural needs include well-draining soil, shade to filtered sunlight, and low to moderate water. No disease known to the inventor affects the new *Agapanthus* variety named 'GOLD STRIKE', however, protection from slugs and snails is recommended. 'GOLD STRIKE' is hardy in USDA Zones 7–10 and reaches 0.45 m. in height and width at maturity.

In comparison 'GOLD STRIKE' is distinguishable from the parents in habit, foliage color and flower color. The closest comparison plants are *Agapanthus* 'Tinkerbell' and *Agapanthus* 'Peter Pan'. Foliage color of 'Tinkerbell' is green and white, while foliage color of 'Peter Pan' is green. The new variety named 'GOLD STRIKE' is distinguishable from the comparison plants by green and gold variegated foliage.

'GOLD STRIKE' was first asexually propagated in 1997, in a cultivated area of Hamilton, New Zealand. The inventor conducted asexual propagation using the method of division. Since that time under careful observation, the new variety named 'GOLD STRIKE' been determined fixed, stable and true to type in successive generations of asexual propagation.

SUMMARY OF THE INVENTION

The following traits have been repeatedly observed and represent the distinguishing characteristics of the new *Agapanthus* variety known as 'GOLD STRIKE'. These traits in combination distinguish 'GOLD STRIKE' from all other existing varieties of *Agapanthus* known to the inventor. 'GOLD STRIKE' has not been tested under all possible conditions and phenotypic differences may be observed with variations in environmental, climatic, and cultural conditions, however, without any variance in genotype.

1. 'GOLD STRIKE' exhibits compact habit.
2. 'GOLD STRIKE' exhibits dark-blue flowers on black stems.
3. 'GOLD STRIKE' exhibits green and gold strap-like leaves.
4. 'GOLD STRIKE' yields four to six divisions a year.
5. 'GOLD STRIKE' blooms in spring and summer.
6. 'GOLD STRIKE' is 0.45 m. in height and width at maturity.
7. 'GOLD STRIKE' is hardy in USDA Zones 7–10.
8. 'GOLD STRIKE' requires shade or filtered sunlight, well-draining soil, and low to moderate water.

BRIEF DESCRIPTION OF THE DRAWINGS

The accompanying color drawings illustrate the overall appearance of the new *Agapanthus* variety named 'GOLD STRIKE' showing color as true as it is reasonably possible to obtain in color reproductions of this type. Drawings depict 24-month-old plants grown out-of-doors in Arroyo Grande, Calif. Color in the drawings may differ from color values cited in the detailed botanical description, which accurately describe the actual color of the new *Agapanthus* variety known as 'GOLD STRIKE'.

Drawing labeled

Drawing labeled

Figure 1:
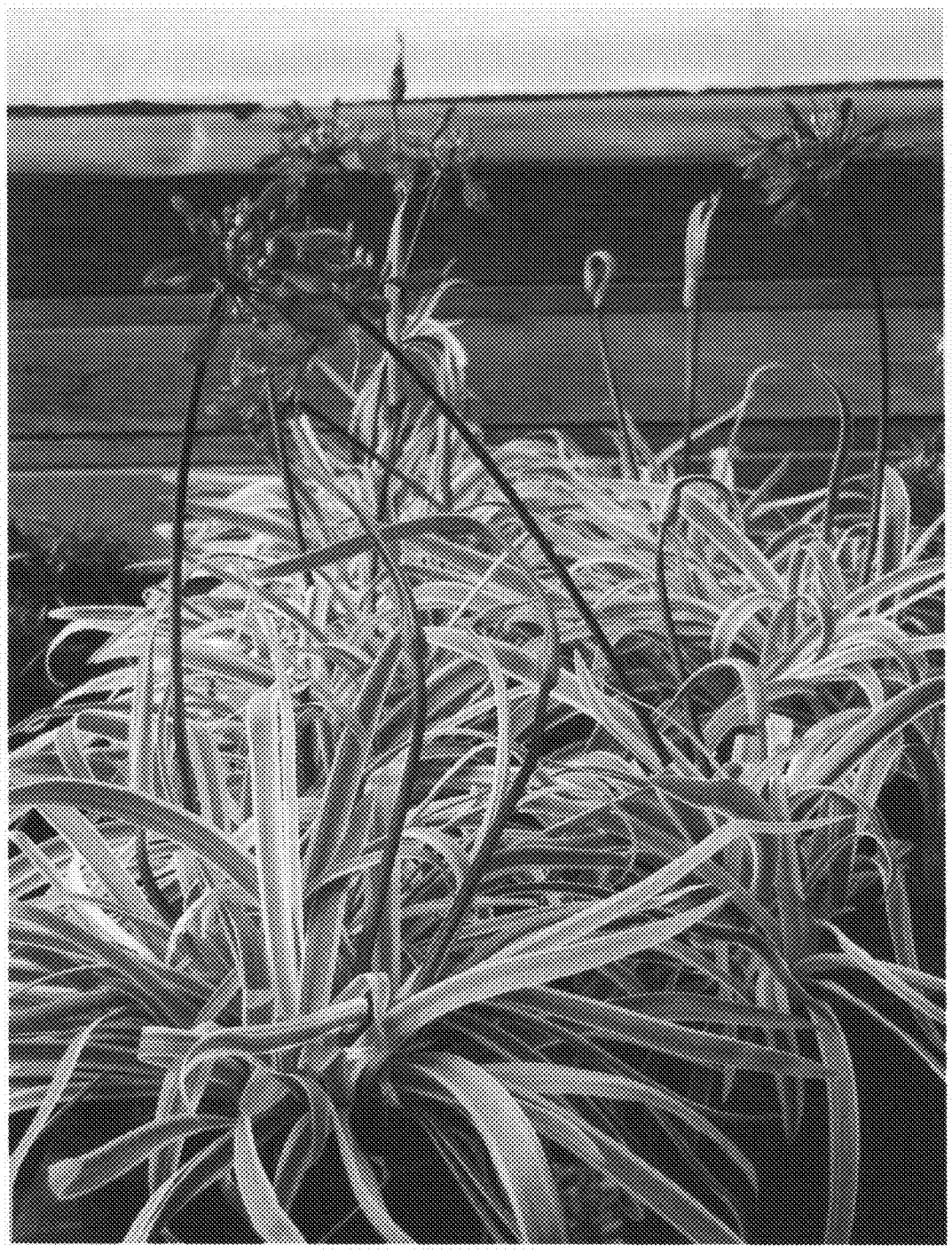
FIG. 1 depicts 'GOLD STRIKE' from a side perspective.
Figure 2:
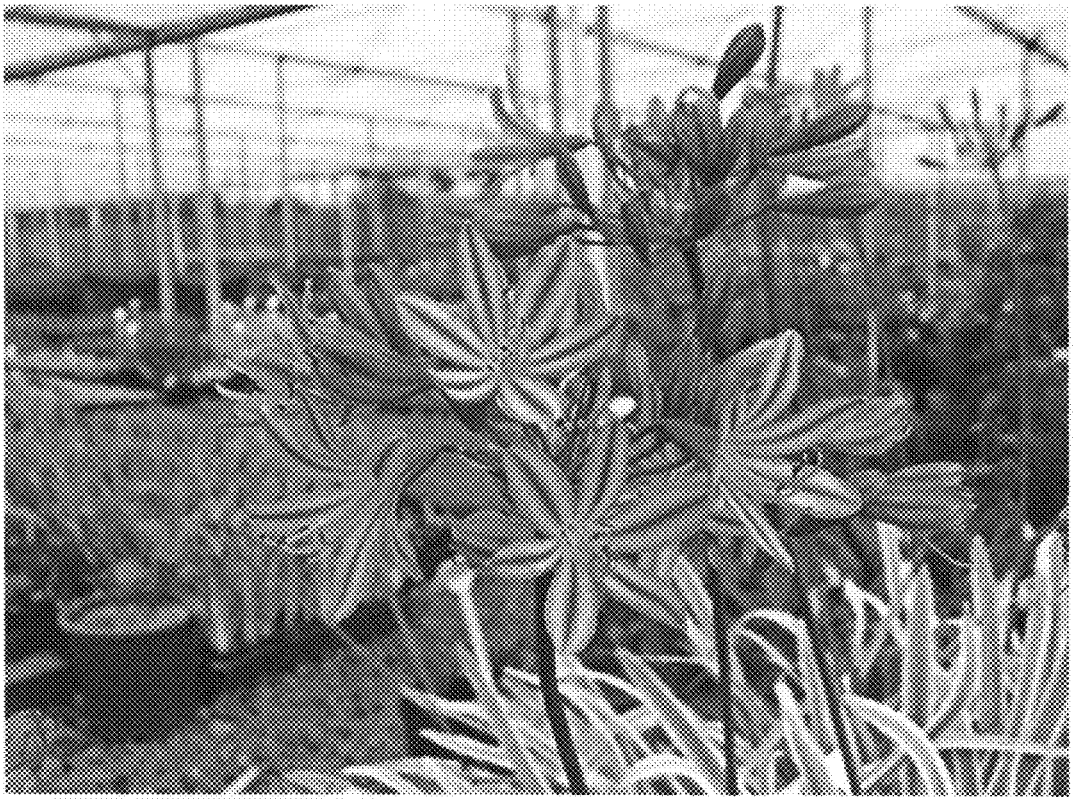
FIG. 2 depicts a close-up view of the inflorescence.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Agapanthus* cultivar named 'GOLD STRIKE'. Data was compiled in Arroyo Grande, Calif. in spring from 24-month-old plants that were originally transplanted into the ground from 1-liter containers. Color determinations are in accordance with the 2001 Royal Horticultural Society Colour Chart except where general color terms of ordinary dictionary significance are used. The growing requirements are similar to the species.

Botanical classification: *Agapanthus inapertus* 'GOLD STRIKE'.
Family: Liliaceae.
Genus: *Agapanthus.*
Species: *inapertus.*
Denomination: 'GOLD STRIKE'.
Common name: Lily-of-the-Nile.
Use: Ornamental for use on deck, patio, and in the landscape.
Type: Perennial herb.
Parentage: *Agapanthus inapertus* 'GOLD STRIKE' is a hybrid that was discovered as a chance seedling resulting from uncontrolled open-pollination of the following parents:
- *Female parent plant.*—An unnamed individual *Agapanthus inapertus.*
- *Male parent plant.*—An unnamed individual *Agapanthus inapertus.*

Vigor: Low.
Habit: Compact.
Plant dimensions (at maturity): 0.45 m. in height and width.
Hardiness: Hardy in USDA Zones 7–10.
Propagation: Asexual propagation is accomplished by division.
Root system: Thick and fleshy.
Cultural requirements: Shade to filtered sunlight, well-draining soil and low to moderate water.
Cropping time (range): 6–9 months to produce a commercial 1-liter container plant from division.
Seasonal interest: Flowers in spring and summer, and variegated foliage year round.
Pests: Protect from slugs and snails.
Disease: None known to the inventor.
Foliage:
- *Foliage type.*—Evergreen.
- *Leaf shape.*—Lorate.
- *Leaf quantity* (*range*).—65–70 leaves per plant.
- *Leaf form.*—Arching.
- *Leaf branching.*—Basal.
- *Leaf attachment.*—Sheathing.
- *Leaf apex.*—Acute.
- *Leaf base.*—Truncate.
- *Leaf division.*—Simple.
- *Leaf margin.*—Entire.
- *Leaf color* (*adaxial surface*).—N137B, N137C, and 11A all individually present.
- *Leaf color* (*abaxial surface*).—N138B, N138C, and 11A all individually present.
- *Leaf surface* (*adaxial and abaxial surfaces*).—Glabrous.
- *Pubescence* (*abaxial and adaxial surfaces*).—None observed.
- *Venation pattern.*—Parallel.
- *Vein color* (*abaxial and adaxial surfaces*).—150D.
- *Leaf dimensions.*—35 cm. in length and 2cm in width.
- *Leaf fragrance.*—None observed.

Inflorescence:
- *Blooming months.*—April through August.
- *Inflorescence type.*—Terminal umbel.
- *Dimensions of inflorescence* (*average*).—11 cm. in diameter and 6.50 cm. in height.
- *Flower quantity* (*average*).—28 flowers per umbel.
- *Persistent or self-cleaning.*—Self-cleaning.
- *Flower aspect.*—Facing upward and outward.
- *Scape quantity* (*range*).—10–12 per plant.
- *Scape shape.*—Cylindrical.
- *Scape texture.*—Pithy.
- *Scape surface.*—Glabrous.
- *Scape color.*—N186A.
- *Scape strength.*—Strong.
- *Scape dimensions.*—34 cm. in length and 0.40 cm. in diameter.
- *Pedicel quantity* (*average*).—28 per inflorescence.
- *Pedicel color.*—N186A.
- *Pedicel dimensions.*—2 cm. in length and 2 mm. in diameter.
- *Pedicel surface.*—Glabrous.
- *Bud shape.*—Obelliptic.
- *Bud color.*—N89D.
- *Bud dimensions* (*average*).—2.50 cm. in length and 0.50 cm. in diameter.
- *Bud apex.*—Rounded.
- *Bud base.*—Cuneate.
- *Bud surface.*—Glabrous.
- *Flower shape.*—Funnel.
- *Flower dimensions.*—3.50 cm. in depth and 3.50 cm. in diameter.
- *Petals.*—Apetalous.
- *Tepals.*—6 in number.
- *Fused or unfused.*—Basally fused.
- *Tepal shape.*—Oblanceolate.
- *Tepal margin.*—Entire.
- *Tepal surfaces* (*abaxial and adaxial*).—Glabrous.
- *Tepal color* (*adaxial surface*).—Ranges between 106B and 106D except central longitudinal stripe 95B.
- *Tepal color* (*abaxial surface*).—95C.
- *Tepal dimensions.*—3 cm. in length and 0.60 cm. in width.
- *Tepal apex.*—Apiculate.
- *Flower fragrance.*—None observed.

Reproductive organs:
- *Stamens.*—6 in number adnate to corolla tube.
- *Stamen color.*—94B.
- *Stamen dimensions.*—3 cm. in length and <2 mm. in diameter.
- *Anther color.*—95A.
- *Anther length.*—1.50 mm.
- *Pollen color.*—161 A.
- *Pollen quantity.*—Low.
- *Pistil.*—One observed.
- *Pistil color.*—94B.
- *Pistil dimensions.*—3 cm. in length and <2 mm. in diameter.
- *Stigma length.*—<1 mm.
- *Stigma color.*—155A.
- *Ovary color.*—11B.
- *Ovary shape.*—Ovoid.
- *Ovary surface.*—Mesic.

*Ovary dimensions*.—0.75 cm. in height and 0.40 cm. in width.

*Ovary position*.—Superior.

Seed: None observed to date.

The invention claimed is:

1. A new and distinct variety of *Agapanthus* plant named 'GOLD STRIKE' as described and illustrated herein.

* * * * *